United States Patent [19]
Endo et al.

[11] Patent Number: 5,351,544
[45] Date of Patent: Oct. 4, 1994

[54] MEASURING APPARATUS USING AN ULTRASONIC WAVE TO PROVIDE FLAKING STATE DETECTION FOR A SPECIMEN ON THE BASIS OF FREQENCY ANALYSIS OF A WAVE REFLECTED BY THE SPECIMEN

[75] Inventors: Tomio Endo; Masahiro Aoki, both of Tokyo; Takeshi Yamagishi, Kanagawa, all of Japan

[73] Assignee: Olympus Optical Co., Ltd, Tokyo, Japan

[21] Appl. No.: 793,615

[22] Filed: Nov. 18, 1991

[30] Foreign Application Priority Data

Nov. 21, 1990 [JP]  Japan .................. 2-318419

[51] Int. Cl.⁵ ............................. G01N 29/12
[52] U.S. Cl. ....................... 73/588; 73/602; 73/609; 73/613
[58] Field of Search .......... 73/602, 606, 588, 630, 73/609, 613

[56]  References Cited
U.S. PATENT DOCUMENTS

| | | | |
|---|---|---|---|
| 4,428,235 | 1/1984 | Sugiyama | 73/602 |
| 4,429,576 | 2/1984 | Norris | 73/609 |
| 4,452,082 | 6/1984 | Miwa | 73/602 |
| 4,655,228 | 4/1987 | Shimura et al. | 73/602 |
| 4,694,699 | 9/1987 | Cheeke | 73/606 |
| 4,893,510 | 1/1990 | Ichikawa et al. | 73/630 |
| 5,029,475 | 7/1991 | Kikuchi et al. | 73/602 |

FOREIGN PATENT DOCUMENTS 3720407  1/1988  Fed. Rep. of Germany .
0257967  2/1990  Japan .

OTHER PUBLICATIONS

"Detection of Smooth Bondings of Polymer Coatings by Ultrasound Spectroscopy", by Y. Tsukahara and K. Ohira, Ultrasonics, 1989 vol. 27. Jan., pp. 3–7.
"Werkstoffprüfung mit Ultraschall" by J. Krautkrämer and H. Krautkrämer, 5th Edition, 1986 pp. 356–359.
"High –Frequency Ultrasonic Testing of Bonds: Application to Silicon Power Devices" by R. S. Gilmore, M. L. Torreno, G. J. Czerw and L. B. Burnet (Materials Evaluation) Jan. 1979 pp. 65–72.
"Ultraschallprüfung an dünner Bauteilen mit Frequenzen über 20 MHz" by E. Neumann, E. Nabel, and K. Matthies (Materialprüf) (Aug. 1978) pp. 291–294.
"Ultrasonic System for imaging delaminations in composite materials", by P. A. Lloyd (Ultrasonics) vol. 27 Jan. 1989 pp. 8–18.

*Primary Examiner*—Hezron E. Williams
*Assistant Examiner*—Rose M. Finley
*Attorney, Agent, or Firm*—Frishauf, Holtz, Goodman & Woodward

[57]  ABSTRACT

A measuring apparatus using an ultrasonic wave according to the invention transmits an ultrasonic wave pulse into a specimen, receives the echo reflected by the specimen and converts it into an electric signal. The components of the electric signal that represent the wave reflected by the specimen and contain data on the state of the specimen are extracted by a gate circuit. The components obtained by the gate circuit are converted into a power spectrum by a circuit for performing a Fourier transformation. The thickness of the specimen and/or the flaking state of the specimen can be determined from this power spectrum.

11 Claims, 12 Drawing Sheets

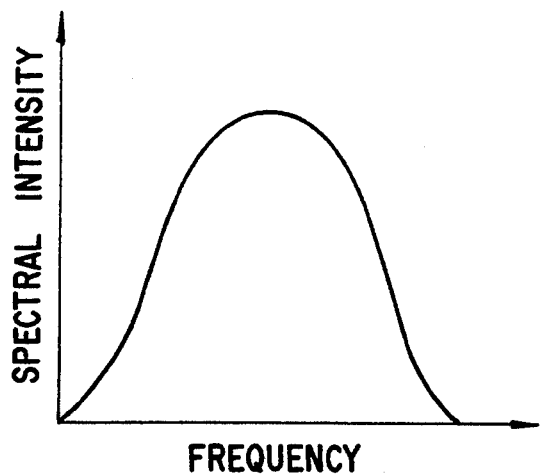
F I G. 6A
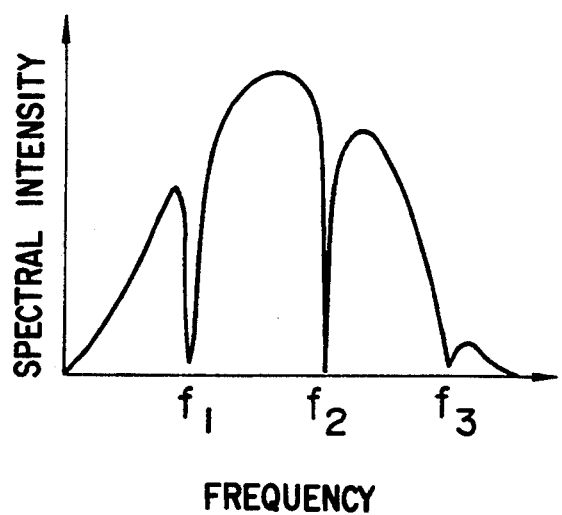
F I G. 6B

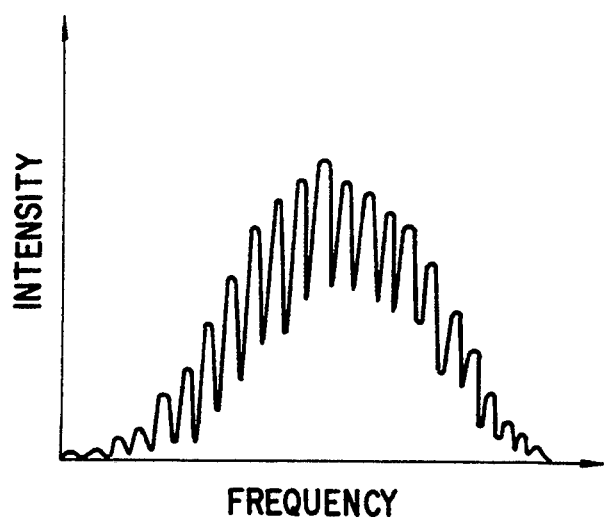
F I G. 10
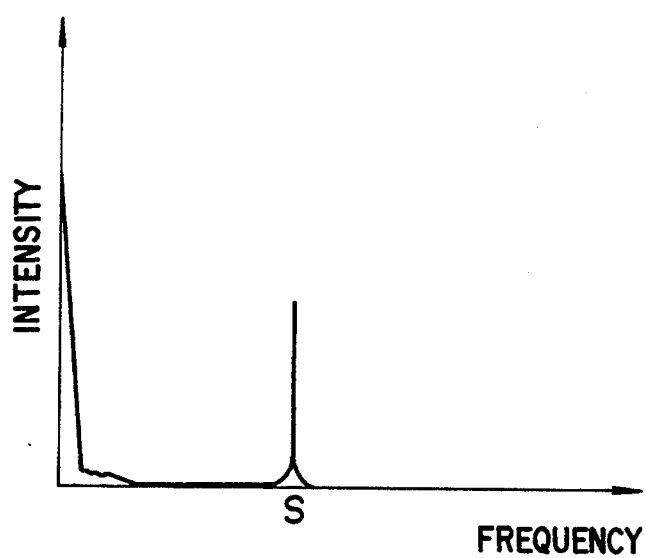
F I G. 11

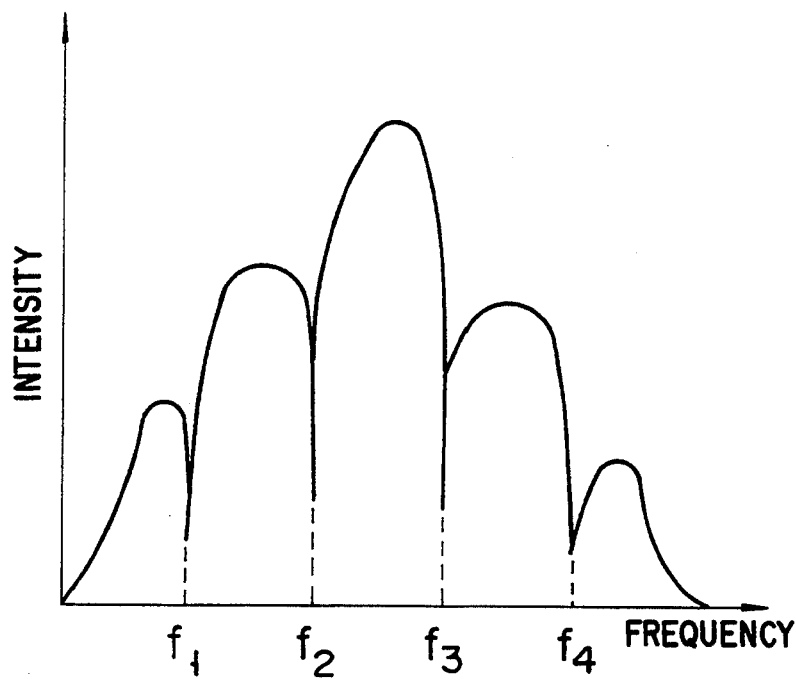
F I G. 12
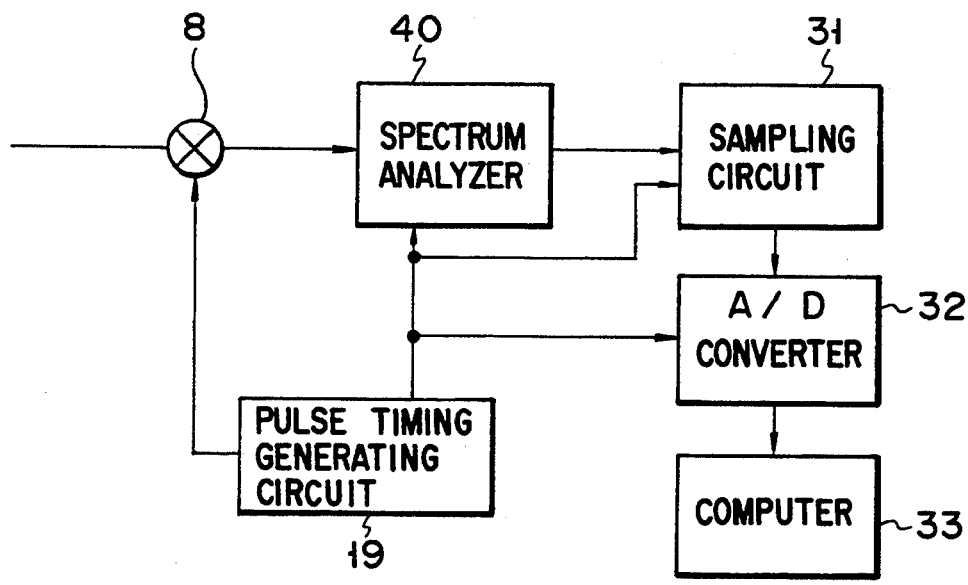
F I G. 13

MEASURING APPARATUS USING AN ULTRASONIC WAVE TO PROVIDE FLAKING STATE DETECTION FOR A SPECIMEN ON THE BASIS OF FREQENCY ANALYSIS OF A WAVE REFLECTED BY THE SPECIMEN

BACKGROUND OF THE INVENTION

1. Field of the Invention

This invention relates to an apparatus for measuring the thickness and/or determining the flaking state of a specimen along its depth by utilizing an ultrasonic wave.

2. Description of the Related Art

Apparatuses using an ultrasonic wave for measurement of various dimensions are already known. An apparatus of this type applies an ultrasonic wave to a specimen, converts the wave (echo) reflected by the specimen into an electric signal, and extracts the component of the electric signal representing the reflected wave from the specimen to determine the condition of the specimen along its depth.

The condition of the specimen determined by such an apparatus normally includes the thickness and/or the state of separation of parts of the specimen.

Now, a known apparatus for determining the flaking state of a specimen along its depth will be described by referring to FIGS. 14, 15A and 15B of the accompanying drawings.

The apparatus comprises a transmitter 51 that generates a single pulse signal at a time. The generated pulse signal is then converted into an ultrasonic wave by a piezoelectric transducer 52, which ultrasonic wave is focused to a minute spot by an acoustic lens 53. A specimen 55 is placed near the focal point of the ultrasonic wave.

Said specimen 55 is mounted on an object stage 56 and the space between the acoustic lens 53 and the specimen 55 is filled with a coupler liquid 54 that transmits the ultrasonic wave.

The ultrasonic wave incident on the specimen 55 is reflected as a function of the acoustic characteristics of the front and back surfaces and the inside of the specimen. The reflected wave then passes the coupler liquid 54, the acoustic lens 53 and is converted into an electric signal by the transducer 52 before it is led to a preamplifier 57.

The output of the preamplifier 57 comprises a number of components that reflect various phenomena involved in the application of the ultrasonic wave including radiation, in-lens reflection, reflection by the front surface of the specimen, reflection inside the specimen and reflection by the back surface of the specimen. The electric signal from the preamplifier 57 containing these components is input to a gate circuit 58. The gate circuit 58 extracts a specific component from those components, and outputs a reflected component signal.

The produced reflected component signals are respectively given to a +detector 59 and a −detector 60. Detector 59 detect a peak level of the entered signal to determine the positive peak intensity of the reflected component signal, while the −detector 60 detects an inverted peak level of the entered signal to determine the negative peak intensity of the signal. The signals detected by the +detector 59 and the −detector 60 are then sent to a comparator 63.

A reflected component signal obtained from a spot of the specimen where IC chips and/or other parts are firmly held together typically shows a waveform as shown in FIG. 15A. When the value of the positive peak is Va+ and the absolute value of the negative peak is Va−, they always hold a relationship as expressed below.

$$Va^+ < Va^- \tag{1}$$

On the other hand, a reflected component signal corresponding to a spot where separation of parts exists shows a waveform shown in FIG. 15B and having a phase shifted by $\pi$ from that of the waveform for a firm spot (without separation of parts) as shown in FIG. 15A. When the value of the positive peak is Vb+ and the absolute value of the negative peak value is Vb−, the two values show a relationship as expressed below.

$$Vb^+ > Vb^- \tag{2}$$

The comparator 63 transmits "1" to a computer 64 when the value for the positive peak is greater than the absolute value for the negative peak, whereas it sends out "0" when the former is smaller than the latter. Output signals from the +detector 59 and those from the −detector 60 are converted into digital signals by respective A/D converters 61a and 61b before being stored in a memory 62.

The data obtained by way of the above operation provide information only for an examined spot in the specimen 55. An XY-scanner 67 scans the specimen 55 on an XY plane by moving the acoustic lens 53 relative to the specimen to bring forth two-dimensional visual data for the specimen, telling where, if any, separated parts are found.

The two-dimensional visual data stored in the memory 62 are then processed by the computer 64, which displays an image of the specimen, emphatically coloring those parts it has judged to be loose and separated from the rest of the specimen in a specific way to make them easily noticeable.

FIG. 16 illustrates a known apparatus for measuring the thickness of a specimen by an ultrasonic wave.

This apparatus comprises a variable frequency oscillator 71 and an ultrasonic probe 72, the output voltage of the oscillator 71 being applied to the ultrasonic probe 72 that performs an electro-acoustic conversion to produce an ultrasonic wave out of the applied voltage. The ultrasonic wave produced by the ultrasonic wave is then applied to a specimen 74 throw a coupler liquid 73.

The wave reflected by the specimen 74 is then brought back into the ultrasonic probe 72 by way of the coupler liquid 73 and converted by the probe into a voltage representing the intensity of the reflected wave. Consequently, the level of the current in the oscillator 71 is subjected to changes.

Now, as the frequency of oscillation of the oscillator 71 is varied, the wavelength $\lambda$ of the ultrasonic wave in the specimen changes. When the thickness d of the specimen 74 is equal to the half wavelength multiplied by an integer (n) or $$n\lambda/2 = d, \tag{3}$$

a stationary wave appears in the specimen 74 and resonates. The energy of oscillation of the ultrasonic wave when the resonance takes place is converted into electricity by the probe 73, which is then added to the electric current in the oscillator 71.

The electric current in the oscillator 71 is amplified by an amplifier 75 and displayed on an oscilloscope 76. Thus, as the frequency of oscillation of the oscillator 71 is varied, a waveform as shown in FIG. 17 will appear on the CRT of the oscilloscope 76, exhibiting regularly separated ridges that indicate frequencies where resonance takes place. If the frequencies for the ridges are expressed by f1, f2 ... fn, fn+1, an equation as shown below can be obtained by using the formula (3) above.

$$d = nV/2fn \qquad (4)$$

where V is the velocity of sound. The thickness of a specimen 74 can be determined by the equation (4) above, if n and v are known.

Even if n is not known, the thickness of a specimen 74 can be determined by calculating the difference of two neighboring resonance frequencies and using the formula below.

$$d = V/2(fn+1-fn) \qquad (5)$$

An apparatus for measuring the state of a specimen by means of an ultrasonic wave as described above is, however, accompanied by certain disadvantages, which will be explained below.

The ability of any known apparatus for determining the flaking state of parts of a specimen by using an ultrasonic wave is subject to limitations because the relationship between the positive and negative peak values of an echo wave reflected from a spot in the specimen having parts which are loose and separated from one another can vary depending on the frequency of the single pulse signal applied to the specimen, the resonance frequency of the transducer of the apparatus, the acuteness of resonance of the transducer, the absorption coefficient of the specimen and other factors.

If, for instance, a frequency of or near 30 MHz is used with such an apparatus to determine the condition of separation of parts of a specimen following a common practice and if the absorption coefficient of the specimen is relatively small, the equation (1) will hold true for an echo wave reflected from a firm spot where no separation of parts exist, whereas the equation (2) will be valid for an echo wave reflected from an area where separation of parts is found.

Conversely, however, the equation (2) will hold its validity for an echo wave reflected from an area where separation of parts exists and the equation (1) will hold effective for an echo wave reflected from a spot where no separation of parts is existent if a frequency of or near 50 MHz is involved.

To make the matter worse, equation (1) will be effective for an echo wave reflected from a firm spot when the specimen has a large absorption coefficient even if a frequency of or near 50 MHz is used, whereas equation (2) will hold true for an echo wave reflected from a loose spot where separation of parts exists, a phenomenon quite contrary to an occasion where the absorption coefficient is relatively small.

Thus, such a known apparatus for determining the flaking state of parts of a specimen that shows a significantly variable relationship between the positive and negative peak values of an echo wave reflected from a spot of a specimen to be examined depending on the performance of the transducer of the apparatus, the frequency of the ultrasonic wave applied to the specimen, the level of the absorption coefficient of the specimen for the ultrasonic wave involved and other factors as described above can be used only with a limited frequency range and a specific transducer if the state of separation of parts of the specimen needs to be known accurately and, therefore, has only a poor applicability.

Besides, any known apparatus of the above described type requires a long time for determining the thickness of a specimen by an ultrasonic wave and hence is not good for a quick instrumentation.

This is because the apparatus employs a continuous wave and requires the frequency of the wave to be continuously changed to find out a resonance frequency for each measurement.

Moreover, such a known apparatus is not good for measuring the thickness of a specimen having a partial upheaval or a specimen having uneven upper and/or lower surfaces.

SUMMARY OF THE INVENTION

It is therefore the object of the invention to provide an apparatus for measuring the thickness of a specimen and the flaking state of the specimen along its depth quickly and accurately without being subject to the conditions of instrumentation and those of the specimen.

According to the invention, the above object is achieved by providing a measuring apparatus using an ultrasonic wave. This measuring apparatus comprises an ultrasonic transmitter/receiver circuit for transmitting an ultrasonic wave pulse into a specimen and converting the echo wave reflected from the specimen into an electric signal, a gate circuit for extracting reflected signal components corresponding to a part of the specimen from the electric signal, a spectrum detector circuit for detecting a power spectrum of the reflected components by means of Fourier transformation and a state detector section for determining the state of the specimen along its depth according to a frequency cycle of the power spectrum.

More specifically, the state detector section of the apparatus comprises a first differentiation circuit for differentiating the power spectrum and a flaking state determining section for determining the flaking state of parts of the specimen from the result of the operation of differentiation of said first differentiation circuit.

Alternatively, the state detector section of the apparatus comprises a characteristics detector section for detecting the frequency characteristics of the power spectrum produced by the spectrum detector circuit, and a circuit for determining the thickness of the specimen as the state of the specimen along its depth according to the frequency characteristics and a velocity of sound in said specimen.

When an ultrasonic wave pulse is transmitted into a specimen from an apparatus according to the invention and having an configuration as described above, the reflected signal components is taken out by the gate circuit from the electric signal and subjected to a Fourier transformation to produce a power spectrum showing the frequency characteristics of the reflected signal component.

The power spectrum has a certain periodical feature that reflects the state of the specimen along its depth. Therefore, the state of the specimen along its depth can be determined by observing the periodical aspect of the power spectrum.

The state detector section differentiates the power spectrum obtained by said spectrum detector/transformer circuit by using its first differentiation circuit and the separation determining section determines the flaking state of parts of the specimen from the outcome of said operation of differentiation.

In other words, an apparatus according to the invention does not determine the state of separation of parts of a specimen from the relationship between the positive and negative peak values of the wave reflected by the spot of separation in question but it determines the flaking state of parts of a specimen from the result of the operation of differentiating the frequency characteristics of the reflected wave. This means that it can quickly and accurately determine the state of the specimen along its depth without being subject to the conditions of instrumentation and those of the specimen.

Besides, the state detector section additionally detects the frequency characteristics of the power spectrum obtained by the spectrum detector/transformer circuit by using its characteristics detector section. Then, the thickness of the specimen is determined as part of the information obtained for the state of the specimen along its depth out of the frequency characteristics and a velocity of sound passing through the specimen.

Since a measuring apparatus according to the invention does not continuously change the frequency of the transmitted signal but applies only a single ultrasonic wave pulse to a specimen to determine its depth, the time required for such a measurement is significantly reduced.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 6A is a graph showing the spectral intensity for a spot of a specimen where parts are separated from each other;

FIG. 6B is a graph showing the spectral intensity for a spot of a specimen where no separated parts are observed;

FIG. 10 is a graph showing the power spectrum of a wave produced as a result of mutual interference of two reflected waves from different paths;

FIG. 11 is a graph of a waveform obtained by Fourier transformation of the power spectrum of FIG. 10;

FIG. 12 is a graph of a waveform obtained by fast Fourier transformation of a reflected wave;

FIG. 13 is a block diagram showing a principal portion of a fourth embodiment of the invention;

DETAILED DESCRIPTION OF THE PREFERRED EMBODIMENTS

Now, the present invention will be described in greater detail by way of preferred embodiments of the invention.

A first embodiment of the invention to be described first is designed to determine the flaking state of parts of a specimen along its depth.

Figure 1:
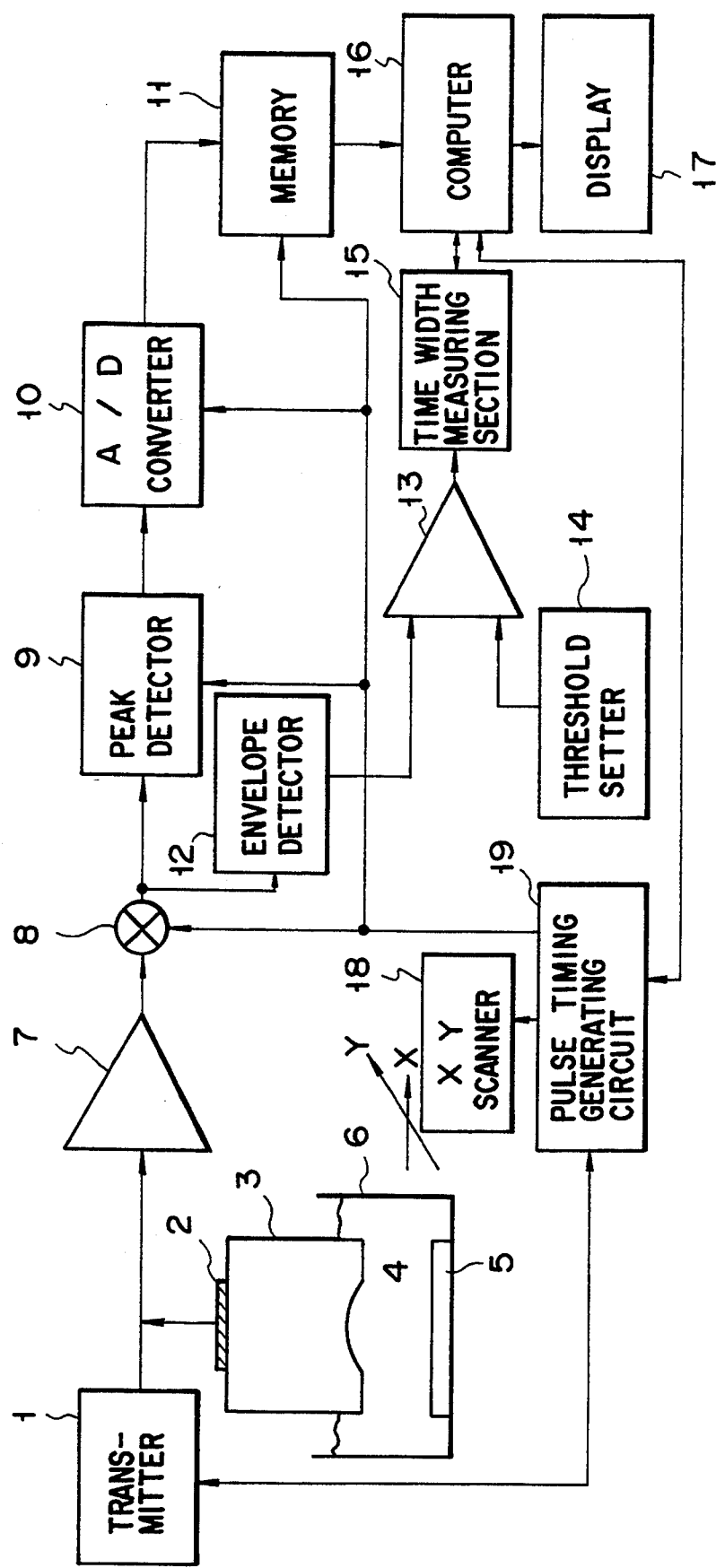
FIG. 1 is a block diagram showing the configuration of a first embodiment of the invention.

FIG. 1 is a block diagram showing the configuration of the first embodiment of the invention that utilizes an ultrasonic wave.

This apparatus comprises an ultrasonic transmitter/receiver section constituted by a transmitter 1 for generating and transmitting an electric single pulse signal, a transducer 2 for converting the pulse signal transmitted from the transmitter 1 into an ultrasonic wave and an acoustic lens 3 for focusing the ultrasonic wave generated by the transducer 2 to a minute spot.

A specimen 5 is placed on a stage 6 which is located near the focal point of the acoustic lens 3. The stage 6 has a side wall to contain a coupler liquid 4 that conveys the ultrasonic wave from the acoustic lens 3 to the specimen 5.

The ultrasonic wave reflected by the specimen 5 passes once again through the coupler liquid 4, the acoustic lens and goes into the transducer 2, where it is converted into an electric signal. A preamplifier 7 is connected to the electric signal output terminal of the transducer 2 to amplify the electric signal and a gate circuit 8 is connected to the output terminal of the preamplifier 7 to take out a reflected signal components from the electric signal which are required for the measurement of the specimen. The output terminal of the gate circuit 8 is connected to a peak detector 9 to detect the peak values of the reflected signal components that have been extracted by the gate circuit 8. The output of the peak detector 9 is converted into a digital signal by A/D converter 10 and stored in a memory 11.

The output terminal of the gate circuit 8 is connected to an envelope detector 12 for detecting envelopes in the reflected and extracted reflected signal component. The output terminal of this envelope detector 12 is connected to one of the input terminals of a comparator 13. The other input terminal of the comparator 13 is input with a threshold value established by a threshold value setting section 14.

The comparator 13 compares the output of the envelope detector 12 and the corresponding threshold value and keeps on sending out its output so long as the level of the reflected signal component exceeds the threshold value and generates a square wave signal having a time-width corresponding to the level of the reflected signal component, The output terminal of the comparator 13 is connected to a time-width measuring section 15, The time-width measuring section 15 measures the time-width of the square wave signal generated by the comparator 13 when its output is turned on and gives the measured value to a computer 16.

The computer 16 has a number of assignments including determining the flaking state of parts at a particular spot of the specimen from the time-width of the square wave signal given by the time-width measuring section 15, reading the image data stored in the memory 11, generating an image of the specimen from the data obtained by the ultrasonic wave probing and emphatically coloring those parts of the specimen in the image it has judged to be loose and separated from the rest of the specimen in a specific way to make them easily noticeable, The computer 16 is connected with a display device 17 for showing an image of the specimen generated by the computer 16 after an ultrasonic wave probing operation and the result of the examination to detect loose and separated parts of the specimen, XY scanner 18 in the diagram scans the specimen 5 on an XY plane by moving the acoustic lens 3 and pulse timing generating circuit 19 controls the timing of the overall operation of the XY scanner 18.

Now, the operation of the embodiment having a configuration as described above will be described by referring to the timing charts shown in FIG. 2. Each time a transmission trigger is given by the pulse timing generating circuit 19 to the transmitter 1, the latter generates a single pulse. The generated single pulse signal is then converted into an ultrasonic wave by the transducer 2 and the ultrasonic wave is converged in the coupler liquid 4 by the acoustic lens 3 and applied to the specimen 5. The ultrasonic wave that has entered the specimen 5 is reflected by various interfaces on and in the specimen 5 including the front and rear surfaces and internal interfaces of elements in the specimen which are acoustically different from each other and the reflected wave is received by the transducer 2 through the acoustic lens 3 and converted into an electric signal, whose amplitude is boosted by the preamplifier 7. The output of the preamplifier 7 contains various reflected signal components, the echo wave including those representing the reflections inside the lens, those by the front and rear surface of and inside the specimen.

Figure 2:
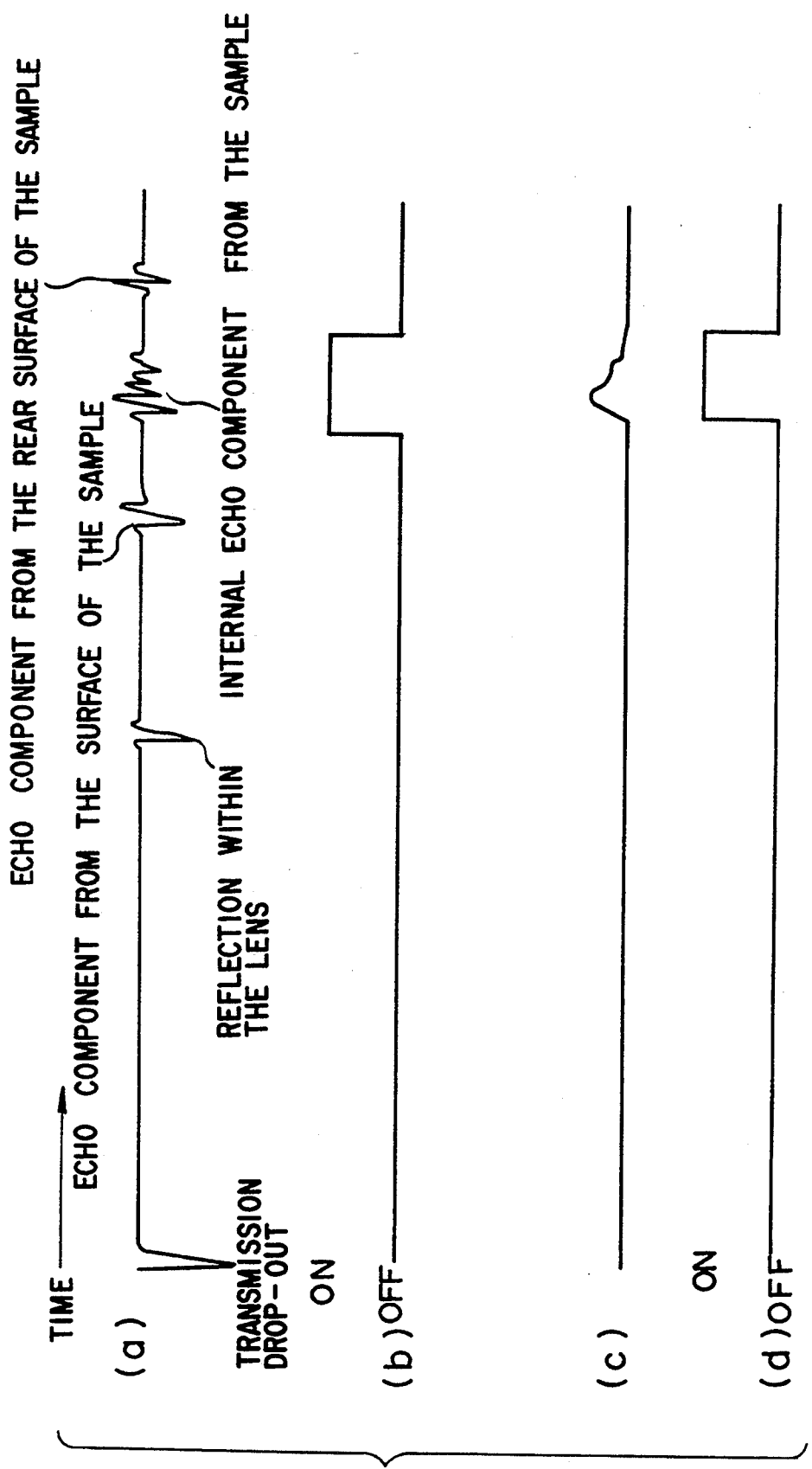
FIG. 2 is a graphic illustration how the embodiment of FIG. 1 operates.

The gate circuit 8 takes out only reflected signal components of the signal that are required for determining the state of separation of parts within the specimen by using a gate signal at a timing which is delayed by a given length of time from the transmission trigger as shown by (b) in FIG. 2.

Figure 3:
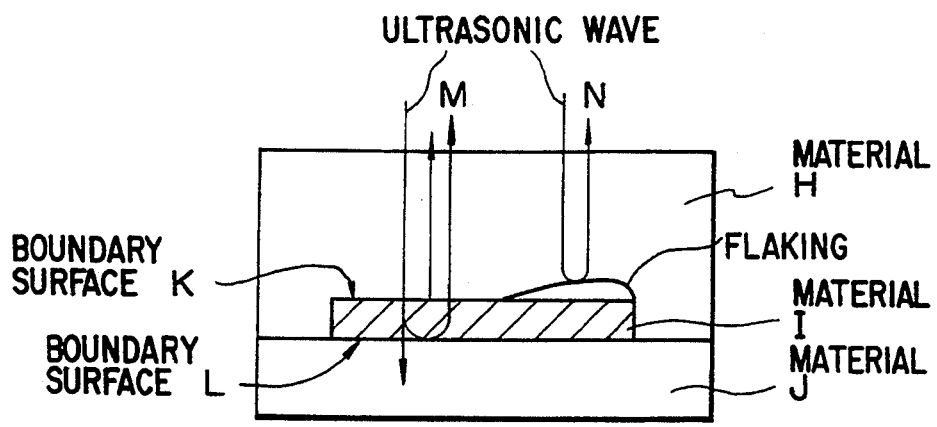
FIG. 3 is a schematic illustration of a specimen showing the path of an ultrasonic wave introduced into the specimen that contains flaking state parts.

Assume that the reflected signal components of the signal that represent the reflections by the boundary surface K are taken out to determine the state of separation of parts along the interface as shown in FIG. 3. The ultrasonic wave from the acoustic lens 3 passes through material H and hits the surface K. At a firm area (where no separation of parts is present), the incident ultrasonic wave is partly reflected by the surface K and part passes through the surface K and eventually reaches the surface L as indicated by M. The ultrasonic wave that has reached the surface L is then partly reflected by the boundary surface and partly passes through there to go into material J.

Figure 4A:
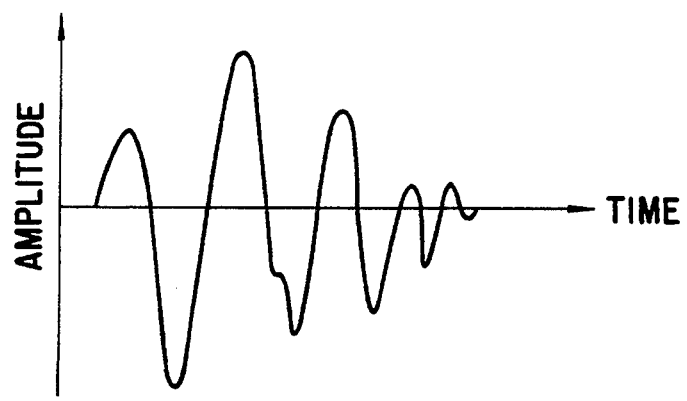
FIG. 4A is a graph showing the waveform of a wave reflected by a firm spot of a specimen.

When a block of material I has a thickness of several hundreds $\mu$m, the wave reflected by the surface K and the wave reflected by the surface L interfere with each other to take a waveform as shown in FIG. 4A.

Figure 4B:
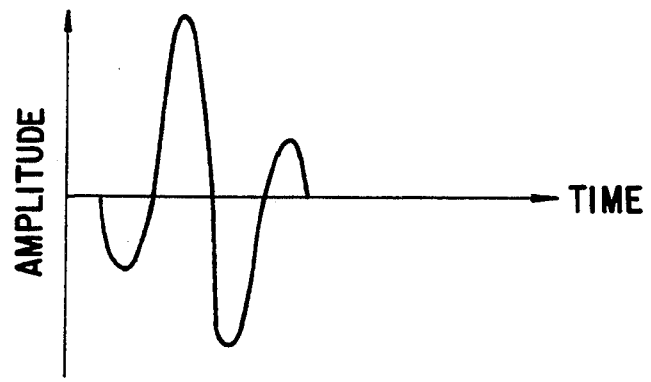
FIG. 4B is a graph showing the waveform of a wave reflected by a loose spot of a specimen where parts are separated from each other.

On the other hand, the ultrasonic that has reached a loose area (where separation of parts exists) is almost totally reflected by the loose area as indicated by N and does not proceed further into the material located below. Therefore, the wave reflected by that area will show a waveform as shown in FIG. 4B. By comparing the waveform of the wave reflected by a firm area (FIG. 4A) and that of the wave reflected by a loose area (FIG. 4B), it will be seen that the wave reflected by a firm area lasts for a relatively long period of time because of the interference of the wave reflected by the firm area and the wave reflected at a lower surface.

The reflected signal component which is taken out by the gate circuit 8 is detected for an envelope by the envelope detector 12 and converted into a signal having a waveform as indicated by (c) in FIG. 2. The signal is then further converted into a square signal as indicated by (d) in FIG. 2 by the comparator 13. The comparator 13 is turned ON when the input signal given to it has a level higher than the value set by the threshold value setting section 14, whereas it is turned OFF when the input signal given to it has a level lower than the value set by the threshold value setting section 14 to consequently generate a square wave as shown by (d) in FIG. 2. The threshold is set to such a level that effectively prevents the output of the comparator 13 from being accidentally made ON by noise while there is no input wave signal to be given to the comparator 13.

The square wave signal produced by the comparator 13 is then measured for its time-width by the time-width measuring section 15 and the measured time-width is given to the computer 16, which determines that there is a separation of parts when the time-width given to it is shorter than a preset time-width which is determined according to the frequency of the ultrasonic wave and the characteristics of the transducer. The predetermined time-width which is a function of the frequency of the ultrasonic wave and the characteristics of the transducer will be typically about 100 ns when the frequency is 30 MHz and about 80 ns when the frequency is 50 MHz.

On the other hand, the output of the gate circuit 8 is also given to the peak detector 9, which detects the peak value. The registered peak value is then converted into a digital value by the A/D converter 10, whose output is stored in the memory 11.

Since a single operation of applying an ultrasonic wave and analyzing the wave reflected by the specimen brings forth data concerning the state of separation of parts for one minute spot hit by the ultrasonic wave, the operation has to be continuously repeated to scan the entire specimen by using the XY scanner 18 if two-dimensional data for the specimen are to be obtained. The acquired two-dimensional data are stored in the memory 11 and then processed by the computer 16, which displays a visual image of the specimen on the display 17, emphatically coloring the separated parts in order to clearly indicate the detected trouble areas.

In short, since this embodiment examines the wave reflected inside the specimen for an envelope and converts, if any, the detected envelope into a square wave, which is then checked for time-width to determine if the ultrasonic wave is reflected by a surface located below the area to be examined for separation of parts, it can determine the state of separation parts without being affected by such factors as the frequency of the ultrasonic wave, the characteristics of the transducer, aberrations caused by the acoustic lens, level of absorption of ultrasonic wave of the coupler liquid and that of the specimen. Therefore, it is free from necessity of changing the frequency of the ultrasonic wave and replacing certain components and consequently able to significantly enhance the overall efficiency of examining specimens. With such features, the embodiment will show an enormous applicability.

Now, a second embodiment of the invention will be described.

Figure 5:
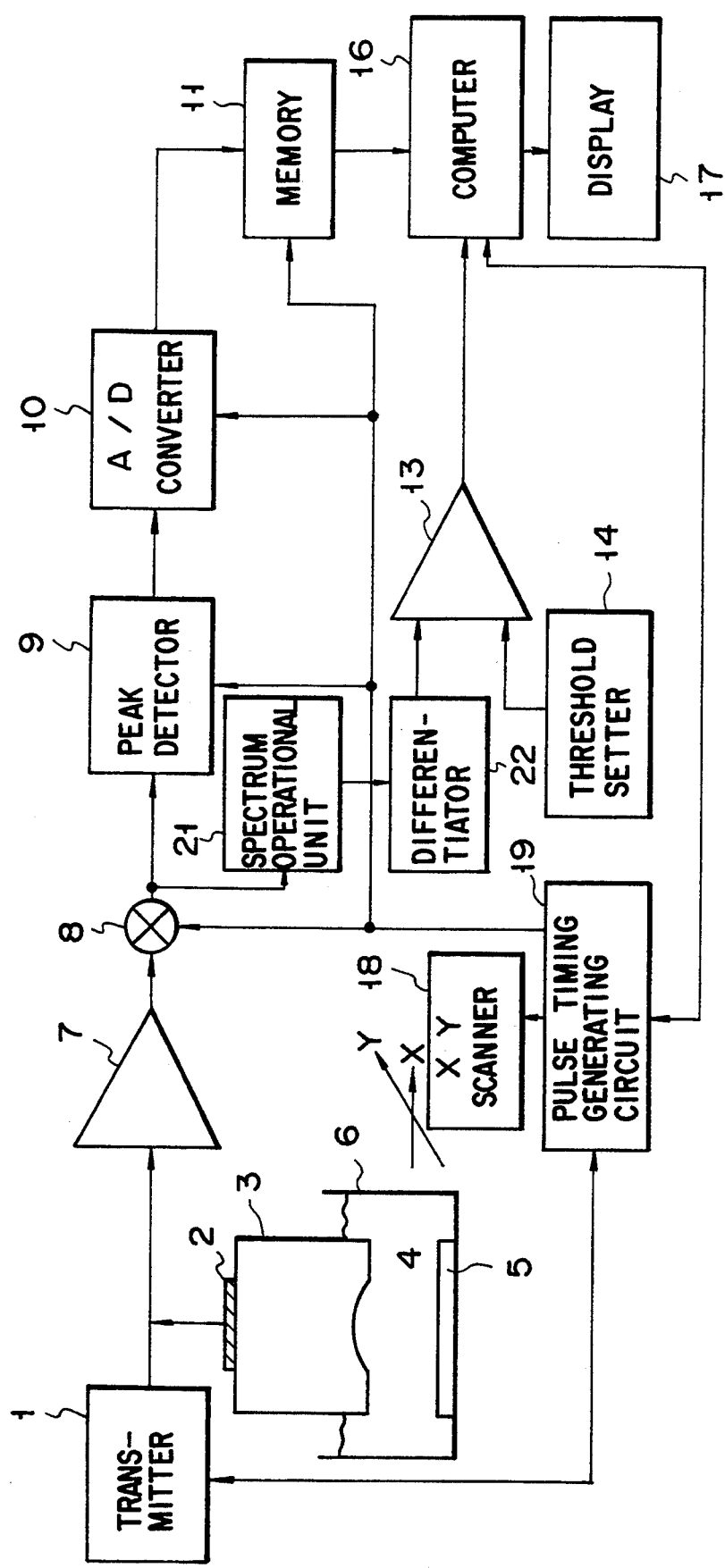
FIG. 5 is a block diagram showing the configuration of a second embodiment of the invention.

FIG. 5 is a block diagram of the second embodiment of the invention.

In this embodiment, those components that are similar to the corresponding ones of the first embodiment will be indicated by the same reference numerals and their explanation will be omitted.

In this embodiment, the output of the gate circuit 8 (reflected signal components) are given to the peak detector 9 as in the case of the first embodiment and, at the same time, to a spectrum operational unit 21. The output of the spectrum operational unit 21 is then differentiated by a differentiator 22, whose output is then given to one of the input terminals of the comparator 13, which compares it with a threshold value set by the threshold value setting section 14 and sends its output to the computer 16.

This embodiment operates in the following way. Like the first embodiment, the gate circuit 8 extracts only reflected signal components corresponding to the wave that are reflected inside the specimen and gives them to the spectrum processor 21 to obtain a frequency spectrum of the components. When there is a flaking state portion in the specimen, the spectrum will typically show a curve that has a maximum point at a certain frequency and rather mountainously increases before and decreases after that point as illustrated in FIG. 6A. When the examined area of the specimen is solid all the way, on the other hand, the incident ultrasonic wave will be partly reflected by the surface K in question and partly by a surface L located directly below the surface to take the route M of FIG. 3 so that the wave reflected by the surface K and the one reflected by the surface L interferes with each other. If the distance between the surfaces K and L is d and the velocity of sound in the material B is V, then the wave reflected by the surface K and the one reflected by the surface L will counteract each other to neutralize their effects when the frequency fn is expressed by the formula below.

$$f_n = nV/2d \qquad (6)$$

$(n = 1, 2, 3, \ldots)$

Thus, the frequency spectrum of the wave reflected by a solid spot will show troughs at the frequencies fn as shown in FIG. 6B. For instance, a wave reflected by a chip in a molded IC will show troughs at frequencies as shown below as the velocity of sound in Si is approximately 8,000 m/s and the chip is normally 0.2 to 0.3 mm thick. Therefore the frequency at the trough is below.

$$f_1 = 20 - 13 \text{ MHz}, f_2 = 40 - 26 \text{ MHz}, \ldots$$

The spectrum obtained by the spectrum operational unit 21 is then differentiated by the differentiator 22. When there is a state of separation of parts in the specimen, the differentiated value of the spectrum will be small as obviously seen from FIG. 6A, whereas it will be very large immediately before and after a trough as may be easily understood from FIG. 6B when the specimen is solid. Therefore, it may be safely said that the specimen is solid when the differentiated value of the spectrum is large, whereas it has a loose area if the differentiated value remains small all the time.

The output of the comparator 13 is kept ON so long as its input is found above a predetermined threshold level set by the threshold value setting section 14 and turned OFF when the input falls below that level. The output signal is then given to the computer 16, which judges that there is a loose area detected by the apparatus when it receives an OFF input signal.

The threshold given to the comparator 13 is set to such a level that effectively prevents the output of the comparator 13 from being accidentally made ON by noise while there is no input wave signal to be given to the comparator 13. As in the case of the first embodiment, the specimen is scanned by the embodiment and the acquired two dimensional data are stored in the memory 11 and then processed by the computer 16, which display a visual image of the specimen on the display 17, emphatically coloring the separated parts in order to clearly indicate the detected trouble areas.

This embodiment brings forth effects similar to those of the first embodiment.

While this embodiment is explained above as it is used to examine throughout a specimen and determine the state of separation of parts in it, it may also be used to check if there is a state of separation of parts at a particular spot of a specimen. If such is the case, a digital oscilloscope may be connected to the output of the gate circuit 8 to take the obtained waveform into the computer 16, which is then subjected to a Fourier transformation, using software, so that any separated parts or not may be determined. Then, a very simple system for detecting separated parts in a specimen can be realized by combining a conventional ultrasonic wave microscope with a digital oscilloscope and software and it will not be affected by the frequency of the ultrasonic wave and the characteristics of the transducer involved.

A third embodiment of the present invention designed to measure the thickness of a specimen will be described below.

Figure 7:
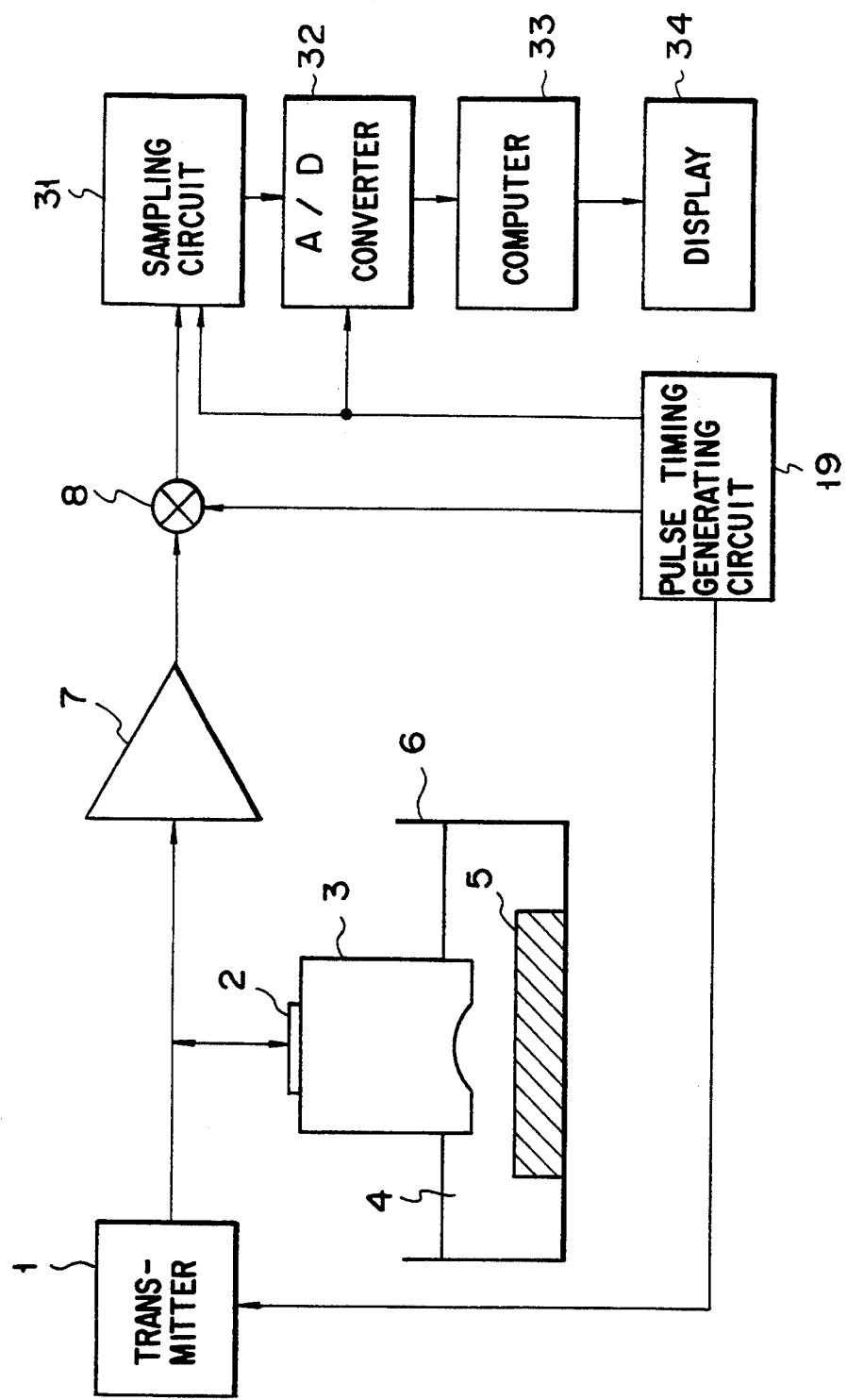
FIG. 7 is a block diagram showing the configuration of a third embodiment of the invention.

FIG. 7 is a block diagram showing the configuration of the third embodiment.

In this embodiment, those components that are similar to the corresponding ones of the first embodiment will be indicated by the same reference numerals and their explanation will be omitted.

In this embodiment, the output terminal of the gate circuit 8 is connected to a sampling section 31, which takes out a sample of the reflected wave. The sampled reflected wave is then converted into a digital signal by an A/D converter 32. The transmitter 1, the gate circuit 8, the sampling section 31 and the A/D converter 32 are connected to the pulse timing generating circuit 19, which sends out a transmission trigger signal to the transmitter 1 to give it a correct timing for transmission. The pulse timing generating circuit 19 also sends a gate trigger signal to the gate circuit 8 and a sampling timing signal to the sampling section 31 and the A/D converter 32 to control the frequency for sampling. The digital signal sent out from the A/D converter 32 is stored in a memory unit of the computer 33.

The computer 33 has a number of assignments including performing Fourier transformations, producing a power spectrum for a specimen through computational operations, determining the frequency characteristics of the obtained power spectrum and then the thickness of the specimen from the frequency characteristics by calculation. The computer 33 is connected with a display device 34 for showing an image of the specimen that contains data concerning the thickness of the specimen.

The embodiment as described above operates in the following manner.

Upon receiving a trigger signal from the pulse timing generating circuit 19, the transmitter 1 generates a single pulse. The generated pulse wave is converted into an ultrasonic wave pulse by the transducer 2. The ultrasonic wave pulse then passes the acoustic lens 3 and the coupler liquid 4 and hits the specimen 5. The wave reflected by the specimen is received by the transducer 2 after passing through the coupler liquid 4 and the acoustic lens. The transducer 2 converts the echo wave into a corresponding electric signal including a reflected component from the specimen. The electric signal is amplified by the preamplifier 7 and then the components of the signal are taken out in a way as described above by referring to the first embodiment.

The reflected signal components taken out by the gate circuit 8 are then converted into a digital signal by the sampling section 31 having a sampling frequency adjusted to greater than double the frequency of the reflected wave and the A/D converter 32 and then given to the computer 33, which determines the thickness of the specimen from the signal.

Now, how the computer operates to determined the thickness of a specimen will be described in detail below. Assume, firstly, an ultrasonic wave is applied from above to material F having a thickness of d and found between material E and material G a shown in FIG. 8. Then, the ultrasonic wave may follow two different routes of reflection, route A for the part of ultrasonic wave reflected by the upper surface of the material F and route B for the part reflected by the lower surface of the material F. If the received wave that comes back through the route A is designated as $C_A(t)$, it will be expressed by the formula below.

$$C_A(t) = R \int SA(f) \sin(2\pi ft) df \qquad (7)$$

where f is a frequency, A(f) is the intensity for each frequency of the incident wave and R is the reflection coefficient of the surface of the materials E and F.

If, on the other hand, the wave following the route B is designated as $C_B(t)$, it will show a phase shift that corresponds to the distance of a double of the thickness d of the material F, or the distance that the wave additionally travels as compared with the wave through the route A. When the attenuation coefficient of the material F is a (f) and the transmission coefficient is S, then the wave $C_B(t)$ passing through the route B will be expressed by the formula below.

$$C_B(t) = \pm \int S/SA(f) e^{-\alpha(f)\cdot 2d} \cdot \sin(2\pi ft + 4\pi f d) df \qquad (8)$$

If the acoustic impedances of the materials E, F and G are ZE, ZF and ZG respectively, the sign of the formula (8) will be either of the following two.

(a) When ZE>ZF>ZC or ZE<ZF<ZC, $C_A(t)$ and $C_B(t)$ have the same phase and $C_B(t)$ has a positive sign.

(b) When ZE>ZF and ZF<ZC or ZE<ZF and ZF<ZC, $C_A(t)$ and $C_B(t)$ have opposite phases and $C_B(t)$ has a negative sign.

From formulas (7) and (8), the wave $C_F(t)$ reflected by the material F will be $$\begin{aligned} C_F(t) &= C_A(t) + C_B(t) \\ &= \int A(f)\{R\sin(2\pi ft) \pm \\ &\quad Se^{-\alpha(f)\cdot 2d} \cdot \sin(2\pi ft + 4\pi f d)\} df \end{aligned} \qquad (9)$$

When sine of the second term has the phase same as that of sine of the first term in the equation (9), the wave will show troughs.

Thus, in the case of (a), because the second term of the equation (9) has a positive sign, peaks appear at $$4\pi(f/V)d = 2n\pi \ (n=1, 2, \ldots) \qquad (10)$$

and troughs appear at $$4\pi(f/V)d = 2(n+1)\pi \ (n=0, 1, 2, \ldots). \qquad (11)$$

From the equation (11) above, the frequencies of troughs are $$f = (2n+1)V/4d \ (n=0, 1, 2, \ldots). \qquad (12)$$

If the frequency for n=0 is fs, the frequencies where troughs appear will be $$fs, 3fs, 5fs, \ldots, (2n+1)fs, \ldots \qquad (13)$$

From the equation (13) above, the thickness of the specimen will be $$d = V/4fs. \qquad (14)$$

In the case of (b), on the other hand, because the second term of the equation (9) has a negative sign, peaks appear at $$4\pi(f/V)d = (2n+1)\pi \ (n=0, 1, 2, \ldots) \qquad (15)$$

and troughs appear at $$4\pi(f/V)d = 2n\pi \ (n=1, 2, \ldots). \qquad (16)$$

From the equation (16) above, the frequencies of the troughs are $$f = 2nV/4d \ (n=1, 2, \ldots) \qquad (17)$$

If the frequency for n=1 is fs, the frequencies where troughs appear will be $$fs, 2fs, 3fs \ldots, nfs, \ldots \quad (18)$$

From the equation (17) above, the thickness of the specimen will be $$d = V/2fs. \quad (19)$$

Figure 8:
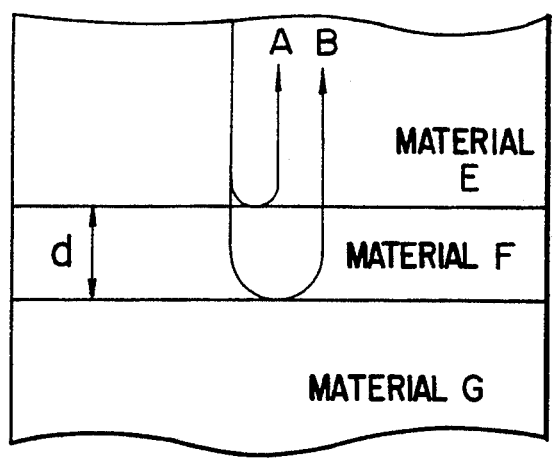
FIG. 8 is a sectional structure of a specimen showing its internal structure.

In this embodiment, the wave reflected by the material F of the specimen having a structure as shown in FIG. 8 is gated and the selected components of the wave are stored in the memory unit of the computer 33.

The components of the reflected wave stored in the memory unit of the computer 33 are then subjected to a fast Fourier transformation to produce a power spectrum of the components as shown in FIG. 12.

The frequency characteristics of the power spectrum can be defined by determining the frequencies f1, f2, f3 and f4 of the troughs of the power spectrum of FIG. 12. This can be done by comparing the intensity of each frequency with that of the adjacent frequency to find out a point where the intensity is greater than the intensity of the adjacent points. Alternatively, the frequency can be determined by differentiating the waveform of the power spectrum, troughs being found at points where the differentiated value changes from negative to positive.

Each of the frequencies f1, f2, f3 and f4 determined in this way is then used as a divisor for dividing a frequency greater than itself, the dividend frequencies being so selected that the quotients of the divisions are always integers. An error of several percent should be taken into consideration for the integers.

When the thickness of the material is small and the velocity of sound passing through it is high, only a trough with a frequency of f1 will appear in the power spectrum. As it is impossible to select a divisor frequency and hence the trough cannot necessarily be discriminated from a trough due to noise in such a case, a method as described below will have to be employed to determine the thickness. For each of the frequencies f1, f2, f3, ..., the differentiated value is examined at and near the frequency to find out the maximum and minimum. Then, the sum of the absolute values of the maximum and minimum is used as the base of evaluation for the frequency. If the corresponding quotient as described above is an integer, the base of evaluation for the frequency that constitutes the numerator of the division is added to the base of evaluation for the frequency that constitutes the denominator of the division.

This calculation is performed each time an integral quotient is obtained as the result of division. If the obtained quotients does not include any odd number, the equation (14) is used for calculation, whereas the equation (19) is used for calculation in any other instances. If there are frequencies each of which is equal to the initial frequency multiplied by an integer, a following averaging operation is performed.

$$fs = \frac{f1 + f2 + f3 + f4}{1 + NINT\left(\frac{f2}{f1}\right) + NINT\left(\frac{f3}{f1}\right) + NINT\left(\frac{f4}{f1}\right)} \quad (20)$$

where NINT signifies a rounding.

When the velocity of sound V in the specimen is known, the thickness of the specimen is determined using either the equation (14) or (19) depending on if (a) or (b) is the case.

Since a single ultrasonic wave pulse is converged to a minute spot by an acoustic lens 3 and then introduced into a specimen 5 so that a power spectrum may be obtained by means of Fourier transformation of the wave reflected by the specimen and the thickness of the specimen may be determined by using the frequencies of the peaks or troughs of intensity of the power spectrum in this embodiment, it can determine the thickness of the specimen by a single transmission of an ultrasonic wave to significantly reduce the time required for measuring the thickness if compared with any conventional measuring apparatus. Moreover, it can measure the thickness of a block of a material inside the specimen. Besides, since it can shoot an ultrasonic wave which is converted to a narrow flux by an acoustic lens 3 and hit any desired spot of a specimen with the flux, it can accurately determine the thickness of a small block of a material without being affected by the unevenness of the surface of the specimen and other adverse conditions.

An alternative method of determining the thickness of a specimen will be used with this embodiment. It will be described below.

The wave $C_A(t)$ that takes the route A and the wave $C_B(t)$ that takes the route B are respectively expressed by the formulas below.

$$C_A(t) = R \int a(f) e^{i2\pi ft} df \quad (21)$$

$$C_B(t) = \pm R'S \int a(f) e^{-\alpha(f) \cdot 2d} \cdot e^{i(2\pi ft - \frac{2\pi f}{V} \cdot 2a)} df \quad (22)$$

If the acoustic impedances of the materials E, F and G are respectively ZE, ZF and ZG, the equation (22) will take a sign as described below.

(a) When ZE>ZF>ZG or ZE<ZF<ZG, $C_B(t)$ takes a positive sign.

(b) when ZE>ZF, ZF<ZG or ZE<ZF, ZF>ZG, $C_B(t)$ takes a negative sign.

From equations (21) and (22), when the reflected waves coming in through the routes A and B interfere with each other to produce a reflected wave C(t) for the specimen, it will be expressed by the equation below.

$$C(t) = \int a(f)\{R \pm SR'e^{-\alpha(f) \cdot 2d} \cdot e^{-i\frac{4\pi + d}{V}}\} \times e^{i2\pi ft} df \quad (23)$$

By performing a Fourier transformation on the equation (23) and if the Fourier transformation of C(t) is $C_F(f)$, $C_F(f)$ will be expressed as follow.

$$C_F(f) = a(f)\{R \pm SR'e^{-\alpha(f) \cdot 2d} \cdot e^{-i\frac{4\pi + d}{V}}\} \quad (24)$$

From the above, the power spectrum of the reflected wave will be expressed by the equation below.

$$|C_F(f)|^2 = \quad (25)$$

$$|a(f)|^2 \left\{ R^2 + S^2 R'^2 e^{-4\alpha(f)d} \pm 2RR'e^{-2\alpha(f)d} \cdot \cos\left(\frac{4\pi f}{4} a\right) \right\}$$

Figure 9:
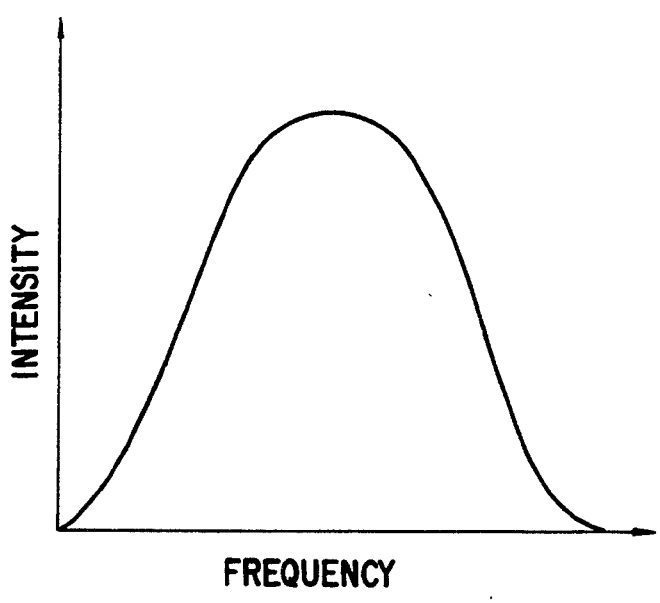
FIG. 9 is a graph showing the relationship between the intensity and the frequency of an incident ultrasonic wave.
Figure 14:
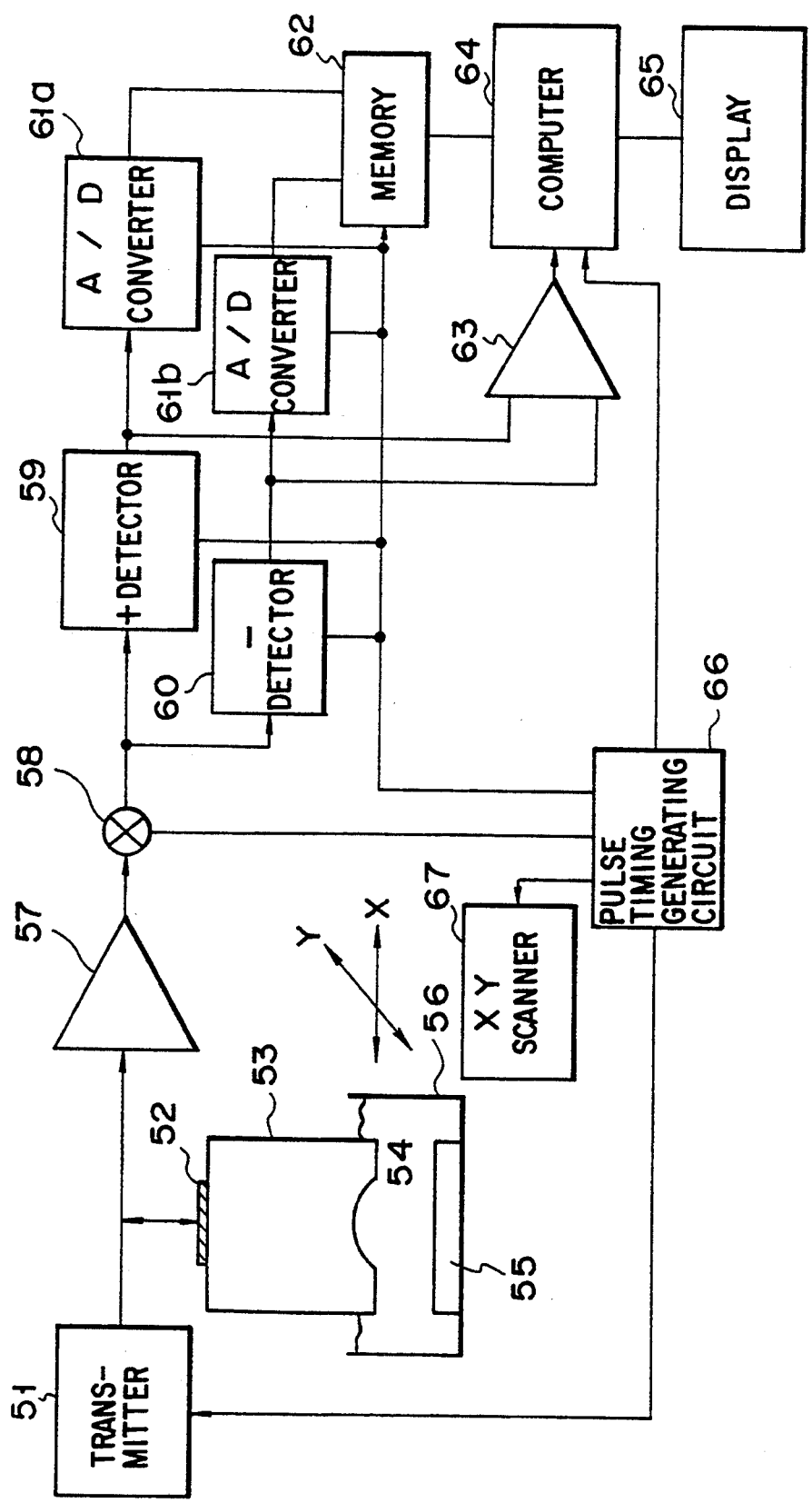
FIG. 14 is a block diagram showing a conventional ultrasonic wave measuring apparatus having a feature of detecting separated parts of a specimen.
Figure 15A:
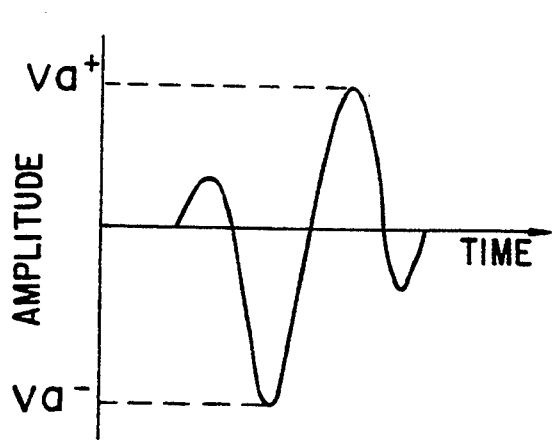
FIG. 15A is a graph showing the waveform of a wave reflected by a firm spot of a specimen.
Figure 15B:
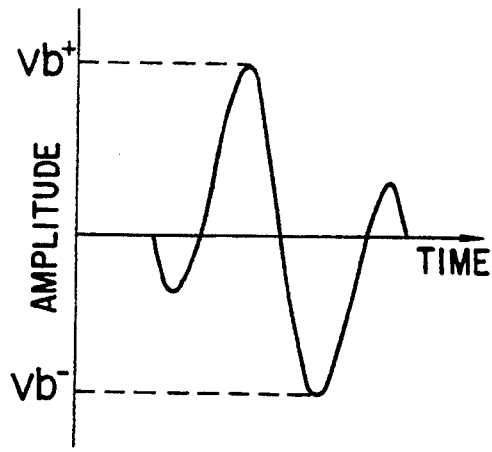
FIG. 15B is a graph showing the waveform of a wave reflected by a loose spot of a specimen where parts are separated from each other.
Figure 16:
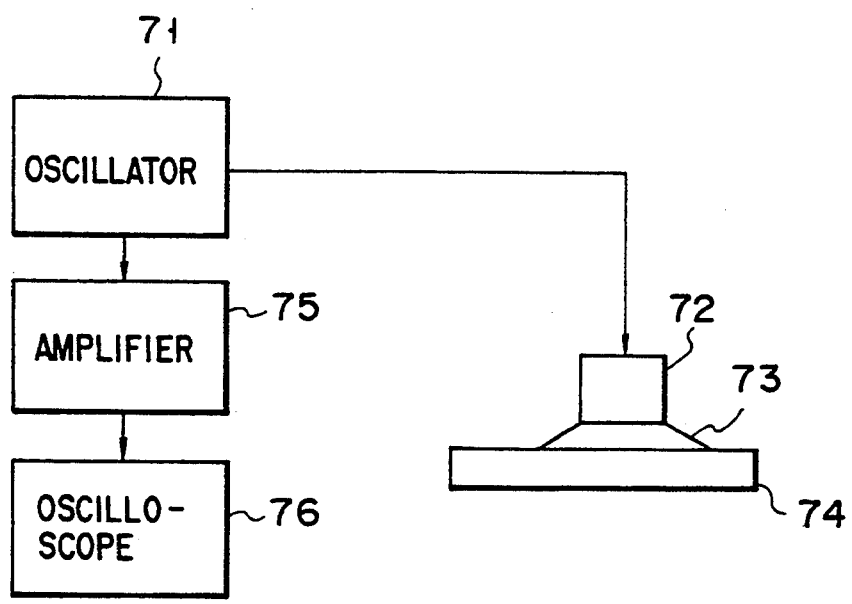
FIG. 16 is a block diagram showing a principal portion of a conventional ultrasonic wave measuring apparatus having a feature of detecting the thickness of a specimen.
Figure 17:
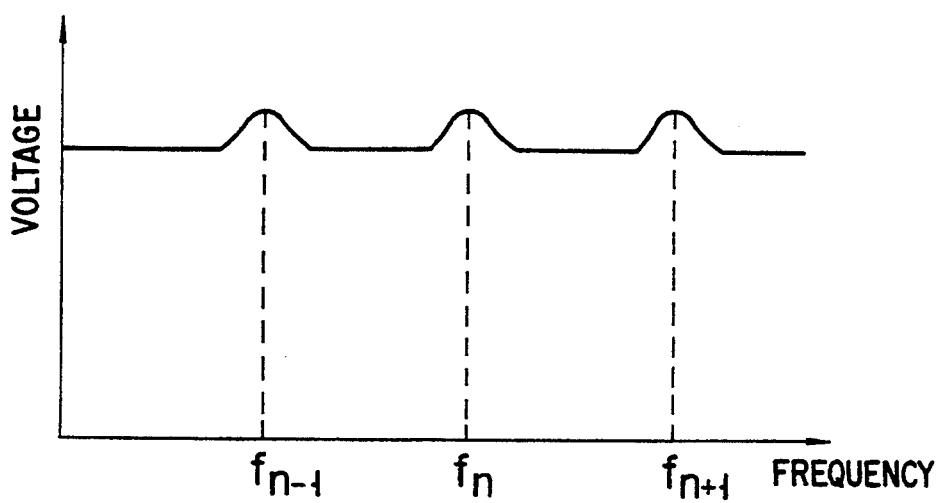
FIG. 17 is a graph illustrating how resonances take place in a specimen as the frequency of a transmitted ultrasonic wave is changed.

$|a(f)|^2$ of the equation (25) represents the intensity of the incident ultrasonic wave as a function of frequency and graphically takes a form as shown in FIG. 9. It is a function that shows a peak at a certain frequency and gradually increases before the peak, whereas it gradually decreases after the peak. It may be understood that $e^{-\alpha(f)\cdot d}$ is a function that monotonously decreases with the increase in the frequency from the fact that a relationship $\alpha(f) \propto 1/f^2$ exists there. The last term of the equation (25) indicates that its value changes periodically with a cycle of $f0 = V/2d$. From these, the power spectrum of the reflected wave realized as a result of interference of the two reflected waves coming in through the respective routes A and B will be a curve as shown in FIG. 10 and produced by superposing a periodic function to the function of FIG. 9.

FIG. 11 shows a graph of a spectrum obtained by a Fourier transformation of the power spectrum of FIG. 10. In FIG. 11, strong peaks appear with a period of S. Since limitations are inevitably imposed to the frequency band for a digital Fourier transformation, the frequency f0 of the cyclic phenomenon in FIG. 10 will be expressed by the following equation if the frequency band for a Fourier transformation is fm.

$$f0 = fm/S \quad (26)$$

From the equation (25), the following equation also holds true.

$$f0 = V/2d \quad (27)$$

Thus, the thickness d of the block of the material F is expressed by the following formula.

$$d = V/2f0 \quad (28)$$

The thickness d can be determined if the speed of sound is known.

Therefore, the computer 33 performs a Fourier transformation on the wave reflected by the specimen to obtain a power spectrum of the reflected wave as shown in FIG. 10 and again a Fourier transformation on the power spectrum to determine the high/low period S of FIG. 11. Thereafter, f0 of FIG. 10 is determined from the high/low period S and the band fm employed at the time of Fourier transformation.

Then, the computer calculates the thickness d from the equation (28) using the determined frequency f0 and the known speed of sound V. The outcome of the calculation is displayed on the screen of the display 34.

Since the value of the frequency f0 of the power spectrum of a wave reflected by a specimen will become large if the specimen to be examined is very thin, the high/low period S of the power spectrum will take a large value to reduce the period of the Fourier transformed power spectrum. This means that the accuracy of measurement of a thin specimen will be inevitably low if digital Fourier transformation is involved because the period has to take an integer.

This problem of low accuracy measurement for a thin specimen may be solved by using a Gauss function or a sink function to determine the peak period by interpolation starting from approximated values for the peak period or, alternatively, by using a maximum entropy method.

Since two Fourier transformations are performed on the same wave reflected by a specimen in the above embodiment, the high/low period S of the power spectrum of the reflected wave can be determined very quickly and easily. Besides, this embodiment is capable of measuring the thickness of a very thin specimen which a conventional apparatus using a single pulse can never measure because of involvement of noise.

While the necessary components of a wave reflected by a specimen is extracted by a gate circuit 8 in the above embodiment, the use of a gate circuit may not be necessary if the waveform of the wave is converted into a digital signal over a wide area and the operation of extracting the required components of the wave is carried out by the computer it comprises.

Finally, a fourth embodiment of the invention will be described by referring to FIG. 13.

This fourth embodiment additionally comprises a spectrum analyzer 40 arranged between the gate circuit 8 and the sampling section 31 of the embodiment of FIG. 7.

The components of the wave reflected by a specimen and extracted by the gate circuit 8 are given to the spectrum analyzer 40, which determines a spectrum for the components by analyzing the waveform of the wave by means of Fourier transformation and sends out the spectrum as its output. The spectrum is then converted into a digital signal by the sampling section 31 and the A/D converter 32 and the obtained signal is given to the computer 33, which performs again a Fourier transformation on the supplied signal and determines the thickness of the specimen, conducting arithmetic operations similar to those of the third embodiment. Note that the computer has to perform only a single Fourier transformation to determine the thickness of the specimen because the signal given to it already takes the form of spectrum data.

This fourth embodiment can determined the thickness of a specimen as accurately as the third embodiment and more quickly than the latter because the computer 33 has to perform only a single Fourier transformation for calculation of the thickness.

While an acoustic lens 12 is used in the third and fourth embodiments to converge an ultrasonic wave to a minute flux, the present invention is not limited thereto and an ultrasonic wave probe which is not a converging type may alternatively be used if the object of examination is only a portion of a specimen or an even area of a specimen. If such is the case, the measurement of the thickness of a specimen can also be carried out very quickly and a very thick specimen which a conventional apparatus cannot measure can be handled so long as these embodiments utilize pulse waves even if they are partly modified.

The waveform or the power spectrum of a wave reflected by a specimen may alternatively be determined by any of the above embodiments after a number of measurements of the wave. The data obtained by these measurements are taken into the computer 33, which then calculates the average of the measurements to determine the thickness of the specimen. This provides an effective way to eliminate adverse effects of noises involved in the process of measurement and consequently enhance the accuracy of measurement.

While the components of a reflected wave that are directly related with the specimen are preliminarily extracted by a gate circuit 8 in the third embodiment, it may alternatively be so configured that it does not comprise a gate circuit and a digital signal containing comprehensive wave data is given firsthand to the computer 33, which thereafter extracts those components that are directly related with the wave reflected by the specimen.

There may be cases where selection of frequencies for troughs is difficult because the power spectrum determined by extracting the necessary components of a reflected wave by means of a gate circuit 8 or a computer 33 contains noise to a large extent. In such a case, the noise contained in the power spectrum can be eliminated by performing a fast Fourier transformation on the power spectrum to cut off the high frequency components from the power spectrum and thereafter an inverse Fourier transformation to restore the power spectrum.

Again, the basic idea of the present invention also provides a way to combine a digital storage oscilloscope or FFT analyzer with a conventional pulse mode ultrasonic microscope or ultrasonic flaw detector normally employed for observation of deep areas of a specimen. Such a combination will offer an easy and effective way of determining the thickness of a specimen if it is used with a software for arithmetic operations of calculating the thickness of a specimen.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A measuring apparatus using an ultrasonic wave, comprising:
   ultrasonic wave transmission/reception means for transmitting an ultrasonic wave pulse into a specimen, for receiving an echo wave from the specimen and for converting the echo wave, including reflected components reflected by the specimen, into an electric signal;
   extracting means for extracting reflected signal components corresponding to the reflected components from the electric signal;
   spectrum detecting means for detecting a power spectrum of the reflected signal components, extracted by said extracting means, on the basis of a Fourier-transformation; and
   flaking detecting means for detecting peaks and troughs of the power spectrum, and for then detecting a flaking of the specimen in accordance with a cycle of the peaks and troughs of the power spectrum that is detected.

2. A measuring apparatus using an ultrasonic wave, comprising:
   ultrasonic wave transmission/reception means for transmitting an ultrasonic wave pulse into a specimen, for receiving an echo wave from the specimen and for converting the echo wave, including reflected components reflected by the specimen, into an electric signal;
   extracting means for extracting reflected signal components corresponding to the reflected components from the electric signal;
   spectrum detecting means for detecting a power spectrum of the reflected signal components extracted by said extracting means; and
   state detecting means for determining a state of the specimen along a depth thereof according to a frequency cycle of said power spectrum, said state detecting means including first differentiation means for differentiating said power spectrum, and flaking state determining means for determining a flaking state of the specimen according to a differentiation result of said first differentiation means.

3. An apparatus according to claim 2, wherein said flaking state determining means includes comparing means for comparing the differentiation result with a preset threshold value to determine the flaking state of said specimen.

4. An apparatus according to claim 3, wherein said comparing means outputs a detection signal for indicating an existence of a flaking portion in the specimen when the differentiation result is smaller than said threshold value.

5. An apparatus according to claim 4, wherein it further comprises:
   scanning means for scanning said specimen by said ultrasonic wave pulse;
   A/D conversion means for converting the reflected signal components extracted by said extracting means to digital data;
   image memory means for storing the digital data representing the reflected signal components as ultrasonic wave image data for said specimen; and
   display means for displaying said ultrasonic wave image data stored in said image memory means and data corresponding to the flaking state determined by said flaking state determining means.

6. A measuring apparatus using an ultrasonic wave, comprising:
   ultrasonic wave transmission/reception means for transmitting an ultrasonic wave pulse into a specimen, for receiving an echo wave from the specimen and for converting the echo wave, including reflected components reflected by the specimen, into an electric signal;
   extracting means for extracting reflected signal components corresponding to the reflected components from the electric signal;
   spectrum detecting means for detecting a power spectrum of the reflected signal components extracted by said extracting means; and
   state detecting means for determining a state of the specimen along a depth thereof according to a frequency cycle of said power spectrum, said state detecting means including characteristics detecting means for detecting frequency characteristics of said power spectrum detected by said spectrum detecting means which correspond to the frequency cycle and means for determining a thickness of the specimen as the state of the specimen along the depth thereof according to said frequency characteristics detected by said characteristics detecting means and a sonic velocity in said specimen.

7. An apparatus according to claim 6, wherein said characteristics detecting means includes differentiation means for differentiating said power spectrum to detect said frequency characteristics of said power spectrum.

8. An apparatus according to claim 6, wherein said characteristics detecting means includes Fourier transformation means for Fourier-transforming said power spectrum to detect said frequency characteristics of said power spectrum.

9. An apparatus according to claim 6, wherein said ultrasonic wave transmission/reception means includes an acoustic lens for converging said ultrasonic wave pulse to a spot on the specimen.

10. An apparatus according to claim 9, wherein said ultrasonic wave transmission/reception means further includes pulse transmission means for generating a pulse transmission signal and a transducer for converting said transmission signal coming from said pulse transmission means into an ultrasonic wave pulse, introducing it into said acoustic lens and converting the echo wave reflected by said specimen and received by said acoustic lens into said electric signal.

11. A measuring apparatus using an ultrasonic wave, comprising:

ultrasonic wave transmission/reception means for transmitting an ultrasonic wave pulse into a specimen, for receiving an echo wave from the specimen and for converting the echo wave, including reflected components reflected by the specimen, into an electric signal;

extracting means for extracting reflected signal components corresponding to the reflected components from the electric signal;

spectrum detecting means for detecting a power spectrum of the reflected signal components extracted by said extracting means;

state detecting means for determining a state of the specimen along a depth thereof according to a frequency cycle of said power spectrum;

detecting means for detecting envelopes in the reflected signal components extracted by said extracting means; and time-width determining means for measuring a time-width of an envelope detection signal obtained by said detecting means; and said state detecting means includes means for determining a flaking state of said specimen from said time-width.

\* \* \* \* \*